United States Patent
Shu

(10) Patent No.: US 6,918,517 B2
(45) Date of Patent: Jul. 19, 2005

(54) NOZZLE FOR A SANITARY CLEANSING DEVICE

(76) Inventor: Jui-Hung Shu, No. 46, Alley 26, Lane 271, Yuan-Hua Rd., Chung-Li City, Tao-Yuan Hsien (TW)

( * ) Notice: Subject to any disclaimer, the term of this patent is extended or adjusted under 35 U.S.C. 154(b) by 83 days.

(21) Appl. No.: 10/699,211

(22) Filed: Oct. 30, 2003

(65) Prior Publication Data

US 2005/0006421 A1 Jan. 13, 2005

(30) Foreign Application Priority Data

Jul. 9, 2003 (TW) ........................................ 92212613 U

(51) Int. Cl.⁷ ............................................. A61M 31/00
(52) U.S. Cl. ...................... 222/568; 222/567; 604/275; 604/279; 604/911; 239/461; 239/548
(58) Field of Search ................................. 604/264, 275, 604/279, 523, 537, 911; 222/567, 568; 239/461, 548

(56) References Cited

U.S. PATENT DOCUMENTS

| 845,249 | A | * | 2/1907 | Morris ........................ 604/275 |
| 2,356,659 | A | * | 8/1944 | De Paiva Aguiar .......... 604/275 |
| 2,386,001 | A | * | 10/1945 | Parrigin ........................ 604/41 |
| 3,916,896 | A | * | 11/1975 | Ballard ........................ 604/279 |
| 4,133,313 | A | * | 1/1979 | Sneider ........................ 604/911 |
| 4,519,794 | A | * | 5/1985 | Sneider ........................ 604/279 |
| 5,380,300 | A | * | 1/1995 | Pritchard et al. ............ 604/275 |
| 6,235,008 | B1 | * | 5/2001 | Heinzelman et al. ........ 604/279 |
| 6,589,216 | B1 | * | 7/2003 | Abbott et al. ................ 604/279 |

* cited by examiner

Primary Examiner—Kenneth Bomberg
(74) Attorney, Agent, or Firm—Darby & Darby

(57) ABSTRACT

A nozzle for a sanitary cleansing device, includes a coupling member defining an intake port, and a tubular body with an axially extending channel having an inlet communicated with the intake port, and an outlet opposite to the inlet. A plurality of angularly displaced elongated grooves are formed in an outer surrounding surface of the tubular body, and have proximate and distal ends proximate to the inlet and the outlet, respectively. A flow diverting member has a passage communicating the outlet and the proximate ends to enable fluid in the channel to be diverted to flow from the proximate ends towards the distal ends for cleansing the analrectal region. A plurality of ejecting holes are formed adjacent to the distal ends and communicated with the intake port so as to enable the fluid to spray out therefrom for cleansing the perianal region.

4 Claims, 4 Drawing Sheets

NOZZLE FOR A SANITARY CLEANSING DEVICE

CROSS-REFERENCE TO RELATED APPLICATION

This application claims priority of Taiwanese Application No. 092212613, filed on Jul. 9, 2003.

BACKGROUND OF THE INVENTION

1. Field of the Invention

This invention relates to a nozzle, more particularly to a nozzle adapted to be connected to a fluid-supplying tube of a sanitary cleansing device.

2. Description of the Related Art

In a conventional automatic cleansing apparatus utilized in a sanitary device, such as a toilet bowl, a control device is provided to control flow of a cleansing liquid through a douche nozzle for spraying a stream of the cleansing liquid onto the perianal region for cleansing the anus of the user. Since the cleaning liquid is merely sprayed onto the perianal region of the user and cannot reach inside the anus or rectum, the cleansing effect is not satisfactory. In addition, the stream of cleansing liquid causes a feeling of discomfort to the user if an insert end of the douche nozzle is inserted into the anal canal for better cleansing effect.

In U.S. Pat. No. 6,235,008 B1, a nozzle suitable for vaginally administering a douche fluid is disclosed. The nozzle is suitable for connection with a squeeze bottle, and includes a channel which is formed in a tubular body and which terminates at an opening for entry into the channel of a douche fluid, lateral apertures which are communicated with the channel to enable the fluid flowing along the channel to exit the tubular body, and recessed grooves which are formed in an external surface of the tubular body for directing the fluid into the grooves in gentle fluid streams.

SUMMARY OF THE INVENTION

The object of the present invention is to provide an improved nozzle which is adapted to be connected to a fluid-supplying tube of a sanitary cleansing device and which provides a satisfactory cleansing effect without causing discomfort to the user.

According to this invention, the nozzle includes a coupling member, a tubular body and a flow diverting member. The coupling member has an internal coupling surface which is adapted to be coupled with a fluid-supplying tube of a sanitary cleansing device and which defines an intake port therein. The tubular body has an inner surrounding surface which defines a channel that has an inlet and an outlet opposite to each other along an axis. The inlet is fluidly communicated with and is disposed downstream of the intake port so as to enable fluid in the tube to flow along the channel from the inlet to the outlet. The tubular body further has an outer surrounding surface opposite to the inner surrounding surface in radial directions relative to the axis. The outer surrounding surface has a plurality of elongated grooves formed therein which are angularly displaced from one another about the axis. Each of the grooves extends in a longitudinal direction substantially parallel to the axis, and has proximate and distal ends proximate to the outlet and the inlet, respectively. The flow diverting member defines a passage therein. The passage has two regions which are opposite to each other in a radial direction relative to the axis and which are fluidly communicated with the outlet of the channel and the proximate ends of the elongated grooves so as to enable the fluid in the channel to be diverted to flow from the proximate ends towards the distal ends along the elongated grooves in a plurality of fluid streams. The outer surrounding surface of the tubular body has a plurality of ejecting holes which are formed adjacent to the distal ends of the elongated grooves. Each of the ejecting holes extends in the longitudinal direction and is fluidly communicated with the intake port so as to enable the fluid to spray out therefrom in a direction substantially opposite to that of the fluid streams.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
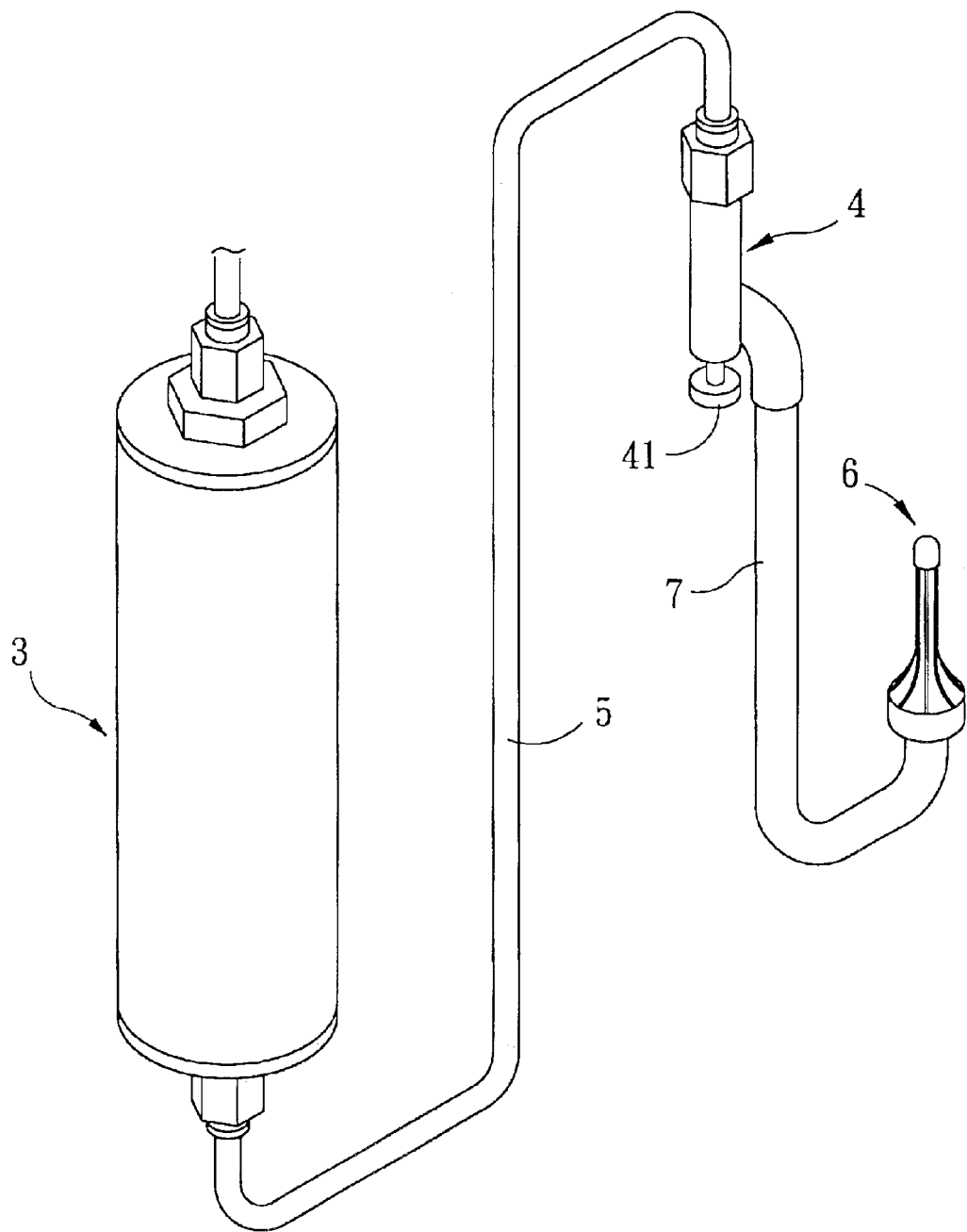
FIG. 1 is a perspective view of the preferred embodiment of a douche nozzle according to this invention when connected to a fluid-supplying tube of a colonic cleansing device.
Figure 3:
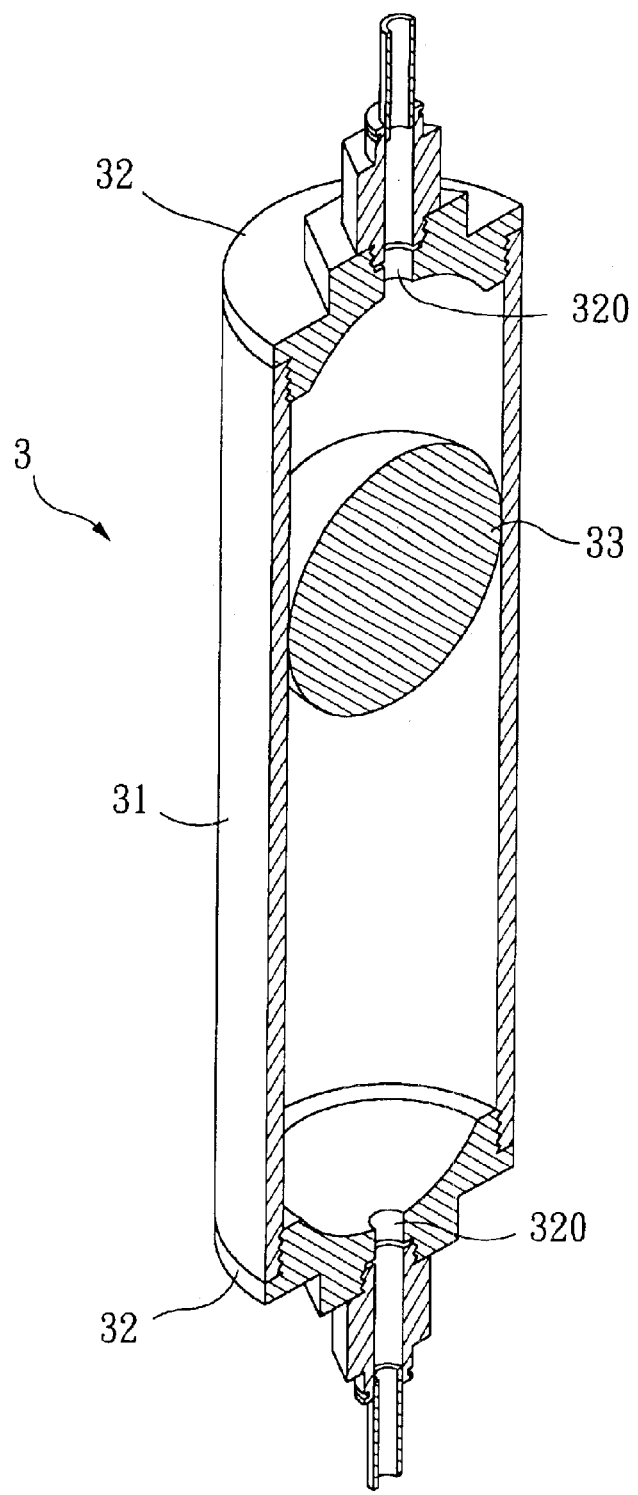
FIG. 3 is a fragmentary, partly sectional perspective view of a valve unit of the colonic cleansing device.

Referring to FIGS. 1 and 3, the preferred embodiment of a douche nozzle 6 according to the present invention is shown to be connected to a flexible fluid-supplying tube 7 of a sanitary cleansing device for cleaning the perianal region and the analrectal parts of the user. The sanitary cleansing device includes a flow control unit 3 which has a cylinder body 31, two end plates 32 which are disposed respectively on two ends of the cylinder body 31 and which respectively have an inlet hole 320 for communicating with a fluid supply (not shown) and an outlet hole 320 for communicating with an actuating unit 4 by means of a pipe 5, and a valve ball 33 which is received in the cylinder body 31. The actuating unit 4 has an actuating member 41 which can be operated to permit the fluid in the fluid reservoir to enter the cylinder body 31 so as to move the valve ball 33, thereby permitting the fluid to flow through the outlet hole 320, the pipe 5, the actuating unit 4 and the tube 7 and to exit through the nozzle 6. In this embodiment, the fluid is clean water.

Figure 2:
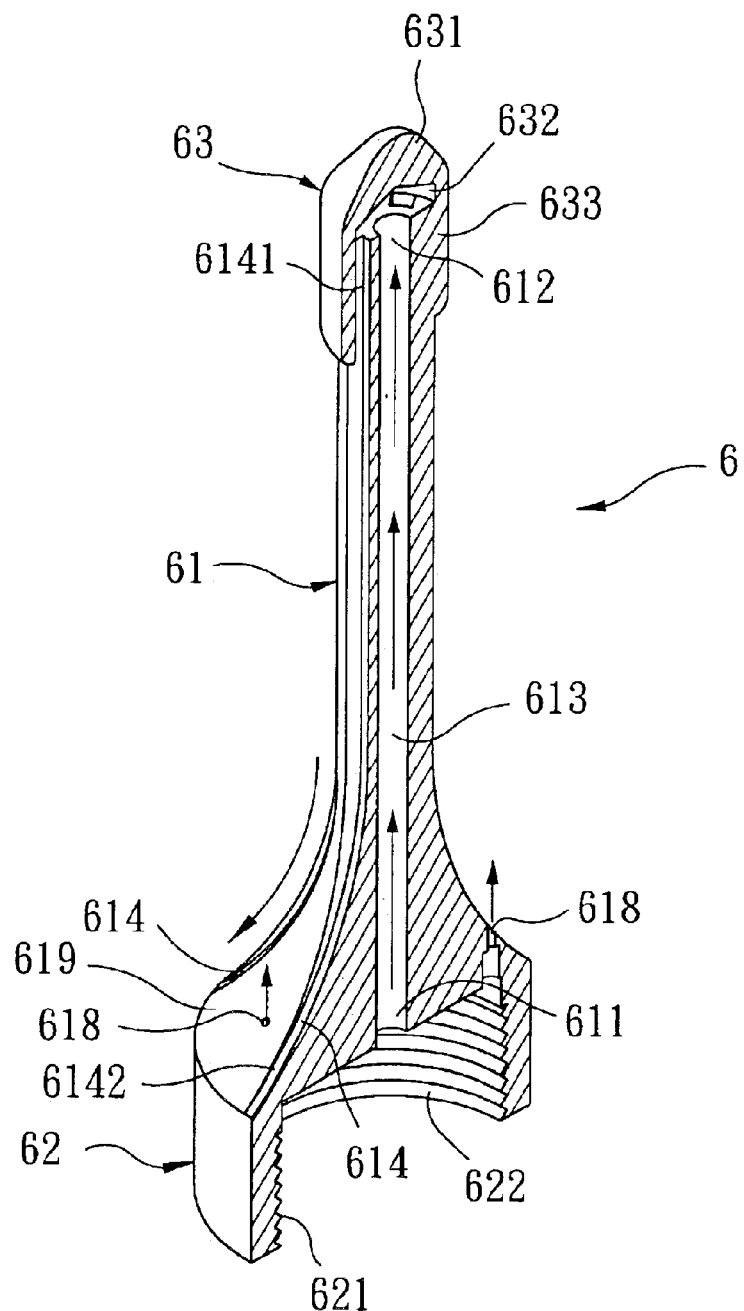
FIG. 2 is a fragmentary, partly sectional perspective view of the preferred embodiment.

Referring to FIG. 2, the nozzle 6 of this embodiment is shown to have an integrally molded one-piece construction, and comprises a coupling member 62, a flow diverting member 63, and a tubular body 61 interposed therebetween.

The coupling member 62 has an internal coupling surface 621 with screw threads. The coupling member 62 is adapted to be coupled with an end of the tube 7 and defines an intake port 622 therein.

The tubular body 61 has an inner surrounding surface which defines a channel 613 that has an inlet 611 and an outlet 612 which are opposite to each other along an axis and which are proximate to the coupling member 62 and the flow diverting member 63, respectively. The inlet 611 is fluidly communicated with and is disposed downstream of the intake port 622 so as to enable the water in the tube 7 (see FIG. 1) to flow along the channel 613 from the inlet 611 to the outlet 612.

The tubular body 61 further has an outer surrounding surface opposite to the inner surrounding surface in radial directions relative to the axis. The outer surrounding surface has a plurality of elongated grooves 614 formed therein which are angularly displaced from one another about the axis. Each of the grooves 614 extends in a longitudinal direction substantially parallel to the axis, and has proximate and distal ends 6141, 6142 proximate to the outlet 612 and the inlet 611, respectively.

Preferably, the coupling member 62 has a cross-section which is larger than that of the tubular body 61 so as to form a shoulder 619 therebetween that flares out towards the coupling member 62.

Furthermore, the outer surrounding surface of the tubular body 61 has a plurality of ejecting holes 618 which are formed adjacent to the shoulder 619. Each of the ejecting holes 618 extends in the longitudinal direction, and is fluidly communicated with the intake port 622 of the coupling member 62 so as to enable the water to spray out therefrom.

The flow diverting member 63 includes a cap wall 631 having a periphery, and disposed to confront the outlet 612 and the proximate ends 6141 of the elongated grooves 614, and a surrounding flange 633 which extends from the periphery of the cap wall 631, which surrounds the axis, and which is sleeved on the outer surrounding surface of the tubular body 61. The cap wall 631 cooperates with the surrounding flange 633 to define a passage 632 which has a central region and a surrounding region opposite to each other in a radial direction relative to the axis. The central region and the surrounding region are fluidly communicated with the outlet 612 of the channel 613 and the proximate ends 6141 of the elongated grooves 614 so as to enable the water in the channel 613 to be diverted to flow from the proximate ends 6141 of the elongated grooves 614 towards the distal ends 6142 along the elongated grooves 614 in a plurality of water streams.

Figure 4:
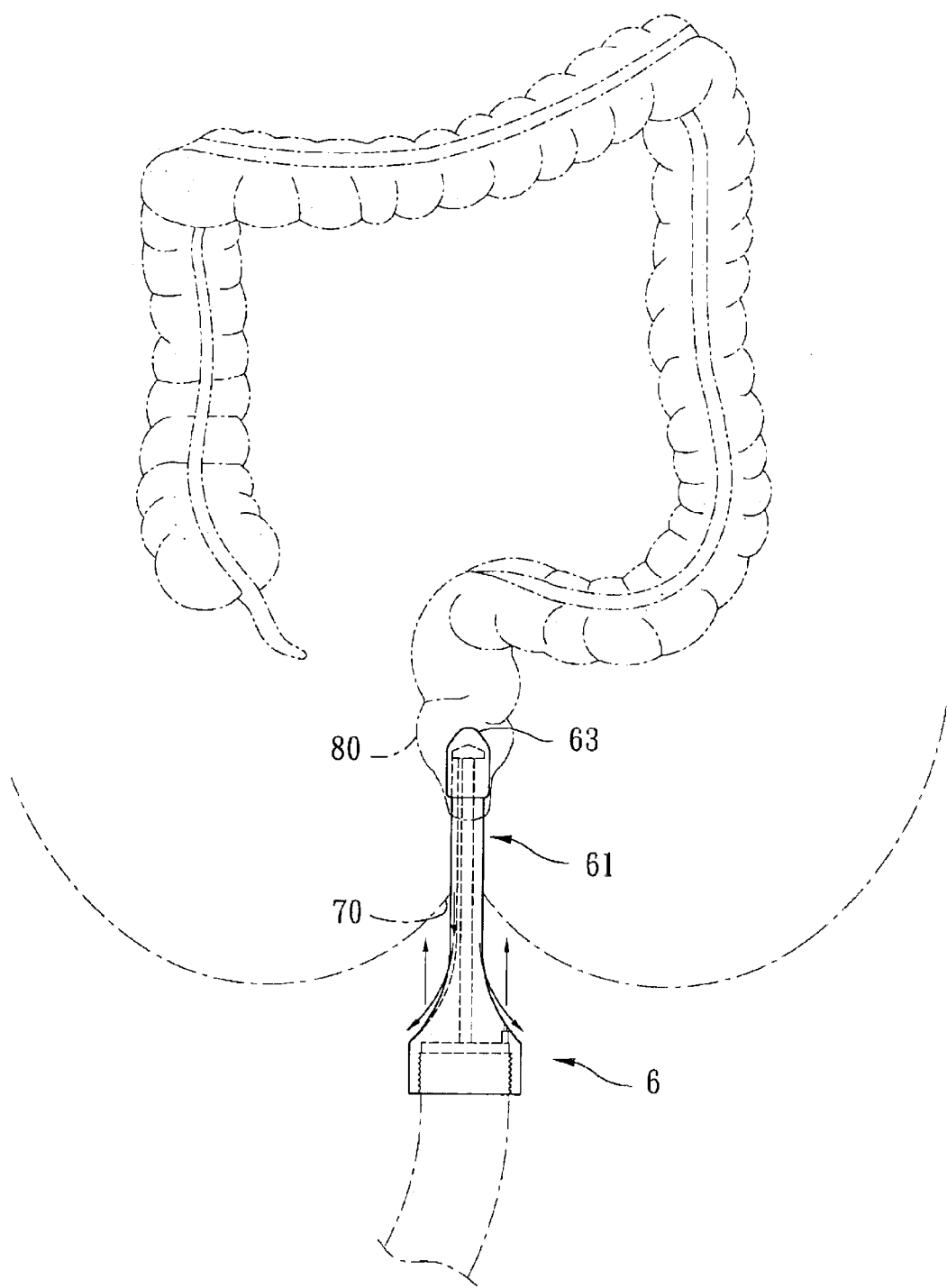
FIG. 4 is a schematic view of the preferred embodiment in a state of use.

In use, with reference to FIG. 4, the flow diverting member 63 is inserted into the anal canal 70, and the actuating member 41 is operated to permit water to flow into the nozzle 6 from the intake port 622. The water flows along the channel 613 to the passage 632 and is then directed to flow along the elongated grooves 614 from the proximate ends 6141 towards the distal ends 6142 in gentle water streams for cleansing the anal canal 70 and the rectum 80. Due to the configuration of the shoulder 619, the waste-mixed water flowing down along the elongated grooves 614 can be easily drained out through the anus.

In the same time, water is sprayed out from the ejecting holes 618 in a direction substantially opposite to that of the water streams flowing along the elongated grooves 614 for cleansing the perianal region.

As illustrated, the nozzle 6 of this invention can provide a plurality of gentle water streams for cleansing the anal canal and the rectum without causing discomfort to the user. In addition, the nozzle 6 can provide a plurality of water jets for cleansing the perianal region of the user.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

I claim:

1. A nozzle adapted to be connected to a fluid-supplying tube of a sanitary cleansing device, comprising:

a coupling member having an internal coupling surface which is adapted to be coupled with the tube and which defines an intake port therein;

a tubular body having an inner surrounding surface which defines a channel that has an inlet and an outlet opposite to each other along an axis, said inlet being fluidly communicated with and being disposed downstream of said intake port so as to enable fluid in the tube to flow along said channel from said inlet to said outlet, said tubular body further having an outer surrounding surface opposite to said inner surrounding surface in radial directions relative to the axis, said outer surrounding surface having a plurality of elongated grooves formed therein which are angularly displaced from one another about the axis, each of said grooves extending in a longitudinal direction substantially parallel to the axis, and having proximate and distal ends proximate to said outlet and said inlet, respectively; and a flow diverting member defining a passage therein, said passage having two regions which are opposite to each other in a radial direction relative to the axis and which are fluidly communicated with said outlet of said channel and said proximate ends of said elongated grooves so as to enable the fluid in said channel to be diverted to flow from said proximate ends towards said distal ends along said elongated grooves in a plurality of fluid streams;

said outer surrounding surface of said tubular body having a plurality of ejecting holes which are formed adjacent to said distal ends of said elongated grooves, each of said ejecting holes extending in the longitudinal direction and being fluidly communicated with said intake port so as to enable the fluid to spray out therefrom in a direction substantially opposite to that of said fluid streams.

2. The nozzle of claim 1, wherein said flow diverting member and said coupling member are formed integrally with said tubular body.

3. The nozzle of claim 2, wherein said coupling member has a cross-section which is larger than that of said tubular body so as to form a shoulder therebetween, said shoulder flaring out towards said coupling member to facilitate draining of the fluid flowing down said elongated grooves.

4. The nozzle of claim 1, wherein said flow diverting member has a cap wall with a periphery, said cap wall being disposed to confront said outlet and said proximate ends of said elongated grooves so as to define said passage, and a surrounding flange which extends from said periphery of said cap wall, which surrounds the axis, and which is sleeved on said outer surrounding surface.

* * * * *